United States Patent [19]

McCann

[11] Patent Number: 5,447,850
[45] Date of Patent: Sep. 5, 1995

[54] METHOD OF PRODUCING METHANE FROM ORGANIC WASTE

[76] Inventor: James L. McCann, 101-1498 Harwood Street, Vancouver, British Columbia, Canada, V6G 1X6

[21] Appl. No.: 188,935

[22] Filed: Jan. 31, 1994

[51] Int. Cl.⁶ ............................ C12P 5/02; C12P 39/00
[52] U.S. Cl. ........................................ 435/42; 435/167; 435/822; 435/911; 435/945
[58] Field of Search ..................... 435/42, 167, 252.1, 435/822, 911, 945

[56] References Cited

U.S. PATENT DOCUMENTS

| | | | |
|---|---|---|---|
| 4,100,023 | 7/1978 | McDonald | 435/167 |
| 4,209,590 | 6/1980 | MacFadden | 435/24 X |
| 4,246,099 | 1/1981 | Gould et al. | 210/603 |
| 4,321,141 | 3/1982 | Messing | 210/603 |
| 4,334,997 | 6/1982 | Peterson | 210/603 |
| 4,481,293 | 11/1984 | Thomsen et al. | 435/167 |
| 4,503,154 | 3/1985 | Paton | 435/167 |
| 4,510,243 | 4/1985 | Haga et al. | 435/167 |
| 4,798,801 | 1/1989 | Hitzman | 435/313 |
| 4,936,996 | 6/1990 | Messing | 435/267 |

*Primary Examiner*—Herbert J. Lilling
*Attorney, Agent, or Firm*—Norman M. Cameron

[57] ABSTRACT

A method of producing methane from organic waste includes the following steps: The waste is first shredded. The waste is inoculated first with aerobic microorganisms. The waste is then fermented with the aerobic microorganisms. Then the waste is inoculated with anaerobic microorganisms. The waste inoculated with anaerobic microorganisms is placed in an oxygen free environment. Methane is then evolved from the waste. Preferably the waste is enriched with nitrogen prior to the anaerobic fermentation.

17 Claims, 7 Drawing Sheets

5,447,850

METHOD OF PRODUCING METHANE FROM ORGANIC WASTE

BACKGROUND OF THE INVENTION

1. Field of the Invention

This invention relates to a method of treating organic waste, particularly urban garbage and a method of producing methane therefrom.

2. Description of Related Art

It is well known that methane is produced as a result of organic material decomposing under anaerobic conditions. In particular, methane is produced and recovered as the result of treating sewage and other waste. However, the amount of methane recovered by present processes is relatively small and of little commercial significance.

The disposal of household garbage has become an increasing problem in North America and throughout the world. Tremendous volumes of such garbage are produced, approximately 500 kilograms per person a year according to some estimates. This garbage contains a high proportion of organic waste such as paper. At present disposal is typically accomplished by trucking garbage to landfill sites where it is compacted and covered with sand or soil. Such sites however become unsightly and can cause contamination of the environment through seepage.

It is an object of the invention to provide an improved method for disposing of household garbage and other organic waste while overcoming the deficiencies associated with landfill sites and other conventional means of disposal.

It is also an object of the invention to provide a method of disposing of household garbage and the like which produces useful by-products.

It is a further object of the invention to provide an improved method of producing methane from organic waste which is significantly more efficient and faster.

It is a still further object of the invention to provide an improved method of producing a useful fuel which preserves the limited resources of petroleum, coal, natural gas and other such resources.

SUMMARY OF THE INVENTION

In accordance with these objects, the invention provides a method of producing methane from organic waste. The waste is shredded and then seeded with aerobic microorganisms. The waste is fermented with the microorganisms. The waste is then inoculated with anaerobic microorganisms. The waste is placed in an oxygen free environment and methane is evolved from the waste. The aerobic microorganisms die and become a nitrogen source for the anaerobic microorganism.

The waste may be placed in a container after being shredded.

Preferably the waste is heated during the aerobic fermentation. For example, the waste may be heated by inoculating the waste with bacillus sub tills.

The waste may be enriched with nitrogen by inoculating the waste with a nitrogen fixer.

The method according to the invention offers significant advantages compared with prior methods of disposing of waste and producing methane. It is capable of handling high volumes of garbage produced by urban areas. The process is safe and the products and by-products are more useful and environmentally more friendly than the initial input of garbage. Significant volumes of methane can be produced which are useful for commercial or industrial applications. This is to be compared with prior art methods of producing methane from waste where barely enough methane is produced to utilize in the process itself. Furthermore, the method requires a capital investment appreciably smaller than that required for some other disposal techniques.

Furthermore, the method does not expose the surrounding area to gaseous emissions as encountered when disposal is achieved by incinerators for example.

DESCRIPTION OF THE PREFERRED EMBODIMENTS

The invention requires a large container which can be sealed from the ambient air. Preferably the structure should be large enough to hold the volume of waste accumulated from two weeks' pick-up. The roof must be airtight yet should be flexible enough to accommodate pressure developed in the structure.

Figure 1:
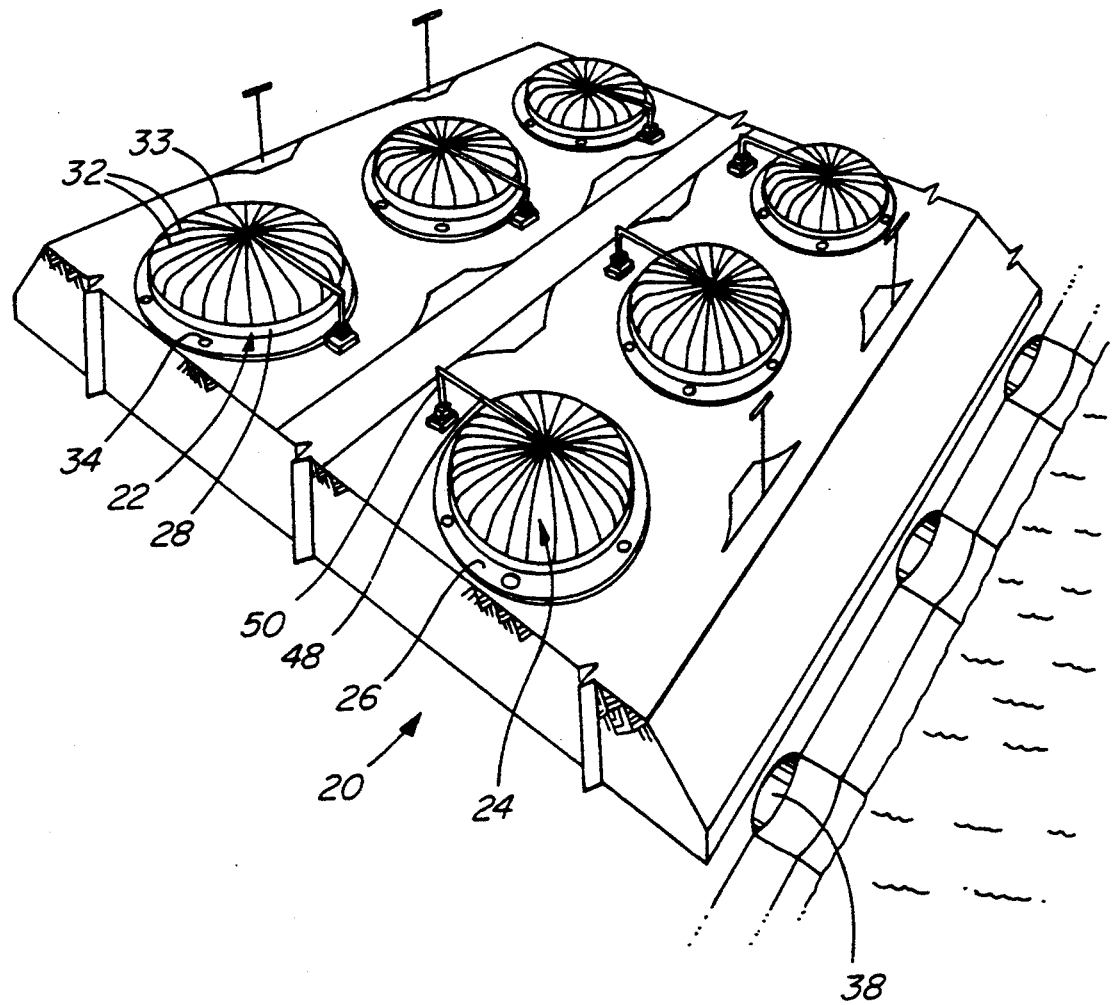
FIG. 1 is a top, front perspective view of an apparatus for producing methane according to an embodiment of the invention.
Figure 2:
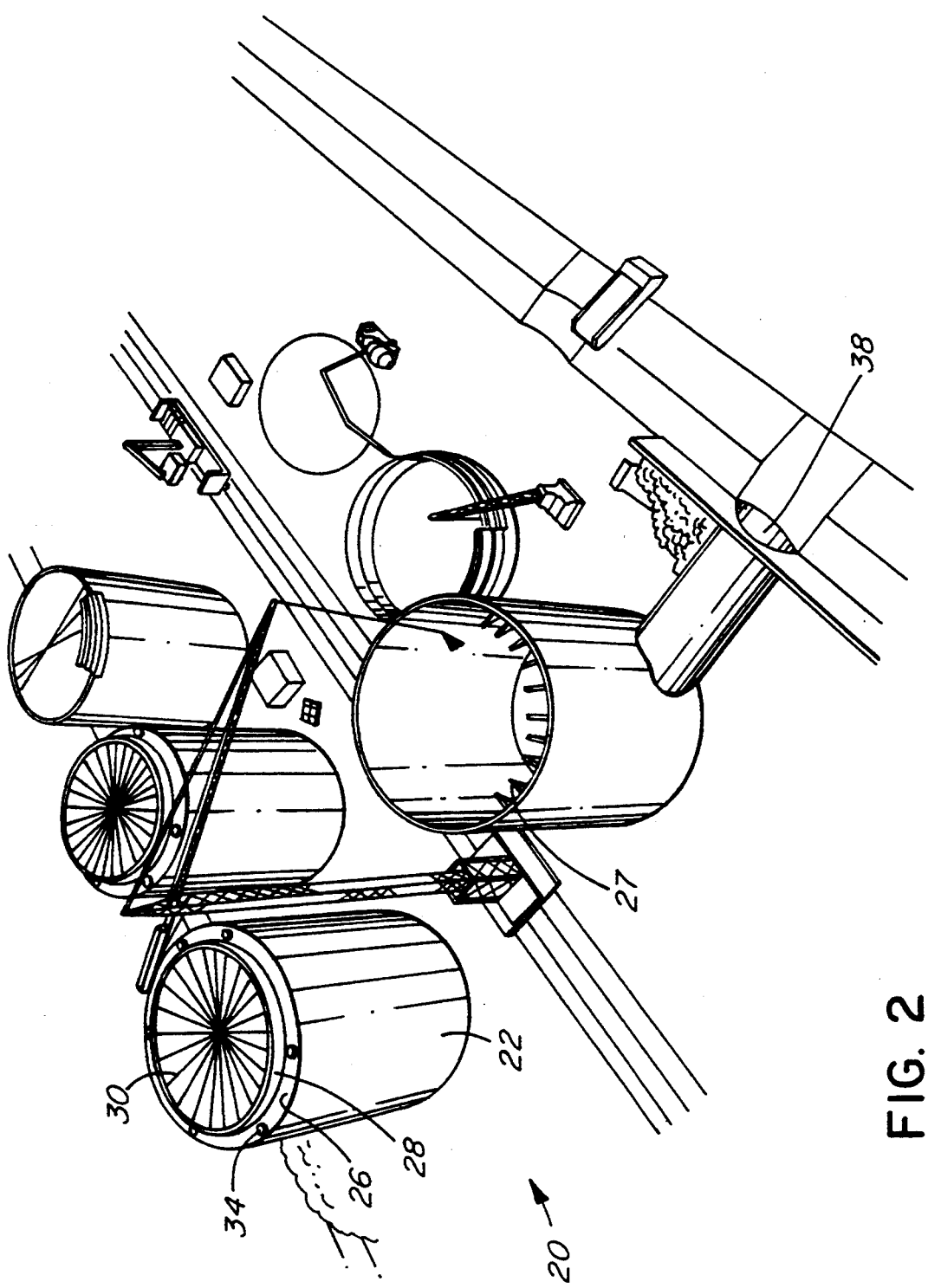
FIG. 2 is a view similar to FIG. 1, showing the apparatus partially constructed.
Figure 3:
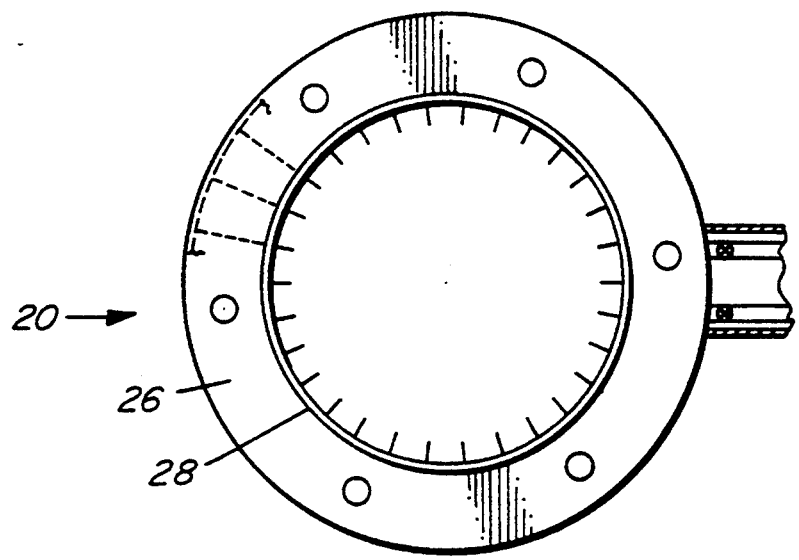
FIG. 3 is a simplified, top plan view of one of the containers thereof with the cover removed.
Figure 4:
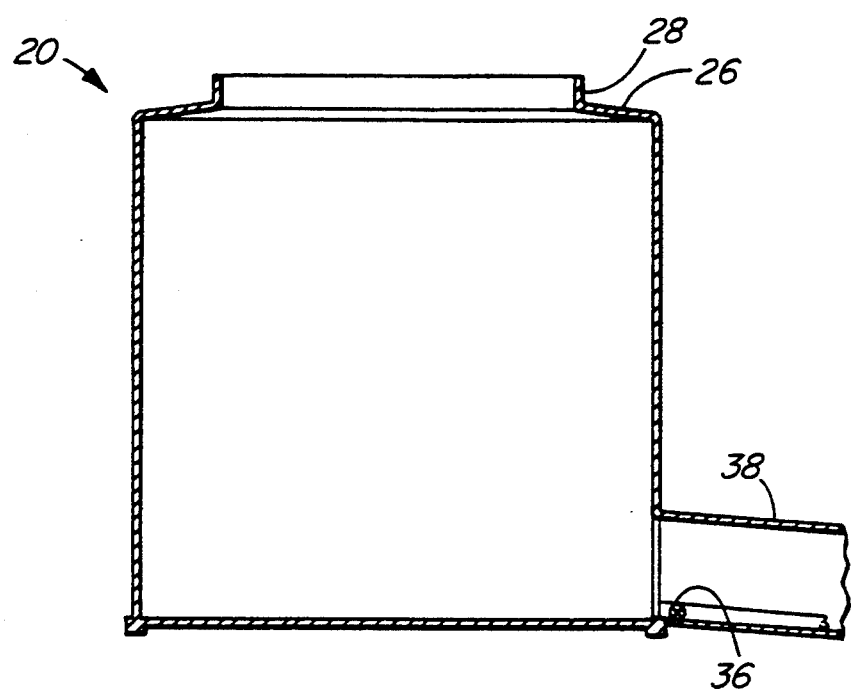
FIG. 4 is a side, sectional view thereof.

FIGS. 1 and 2 show an apparatus 20 for producing methane from organic waste which includes six such containers 22. In the present example each container is in the form of a cylinder of reinforced concrete. Each cylinder in this example is 30 meters in diameter and 30 meters high with a volume of approximately 21,000 cubic meters. The size however can be changed for other embodiments of the invention. FIG. 2 shows the containers 22 with roofs 24, shown in FIG. 1, removed and the containers in different stages of completion.

Figure 5:
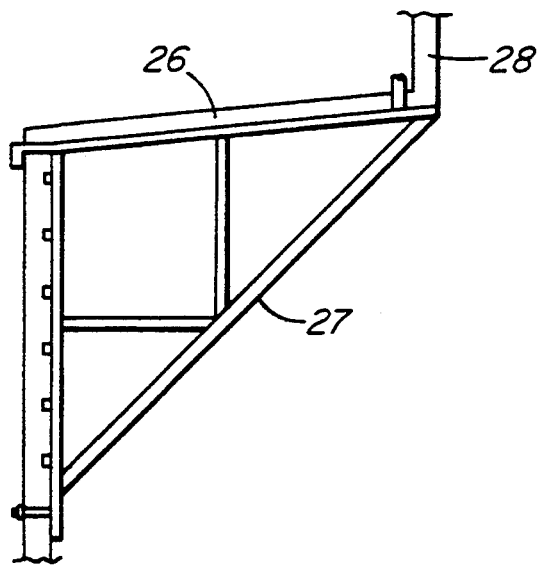
FIG. 5 is an enlarged, fragmentary section of one of the support frames thereof.
Figure 6:
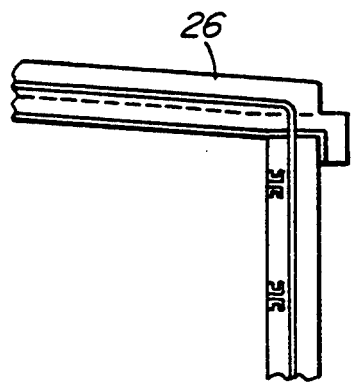
FIG. 6 is an enlarged, fragmentary view showing the joint between one of the steps and the top of one of the containers.

Each roof is formed with a 5.4 meter concrete step 26. The step is supported by a plurality of support frames 27 of structural steel in this example, as seen in FIG. 2 and FIG. 5. The step wall 28 is 1.5 meters high. A support roof is formed by stretching a 1 cm. steel cable 30 between the extending reinforcing rods. The concrete structure is formed by slip forming. These dimensions relate to this preferred embodiment and can be varied in other embodiments as can the specific structure.

Figure 7:
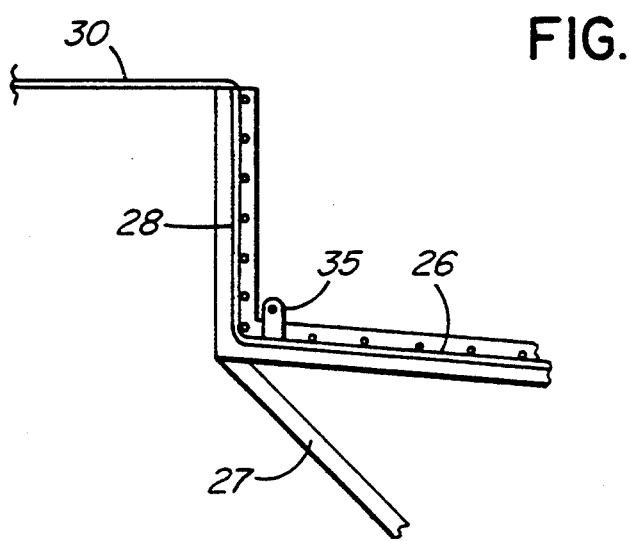
FIG. 7 is an enlarged, fragmentary view showing a portion of one of the support frames, a cable for supporting the roof and the bracket thereof.

The flexible cover 32 is made from glass fiber reinforced polytetrafluoroethylene (PTFE) in this example. The cover is bonded onto the side wall and stabilized with a cable mesh 33 anchored to brackets 35 welded to corner support frames 27 as seen in FIG. 1 and FIG. 7.

Figure 8:
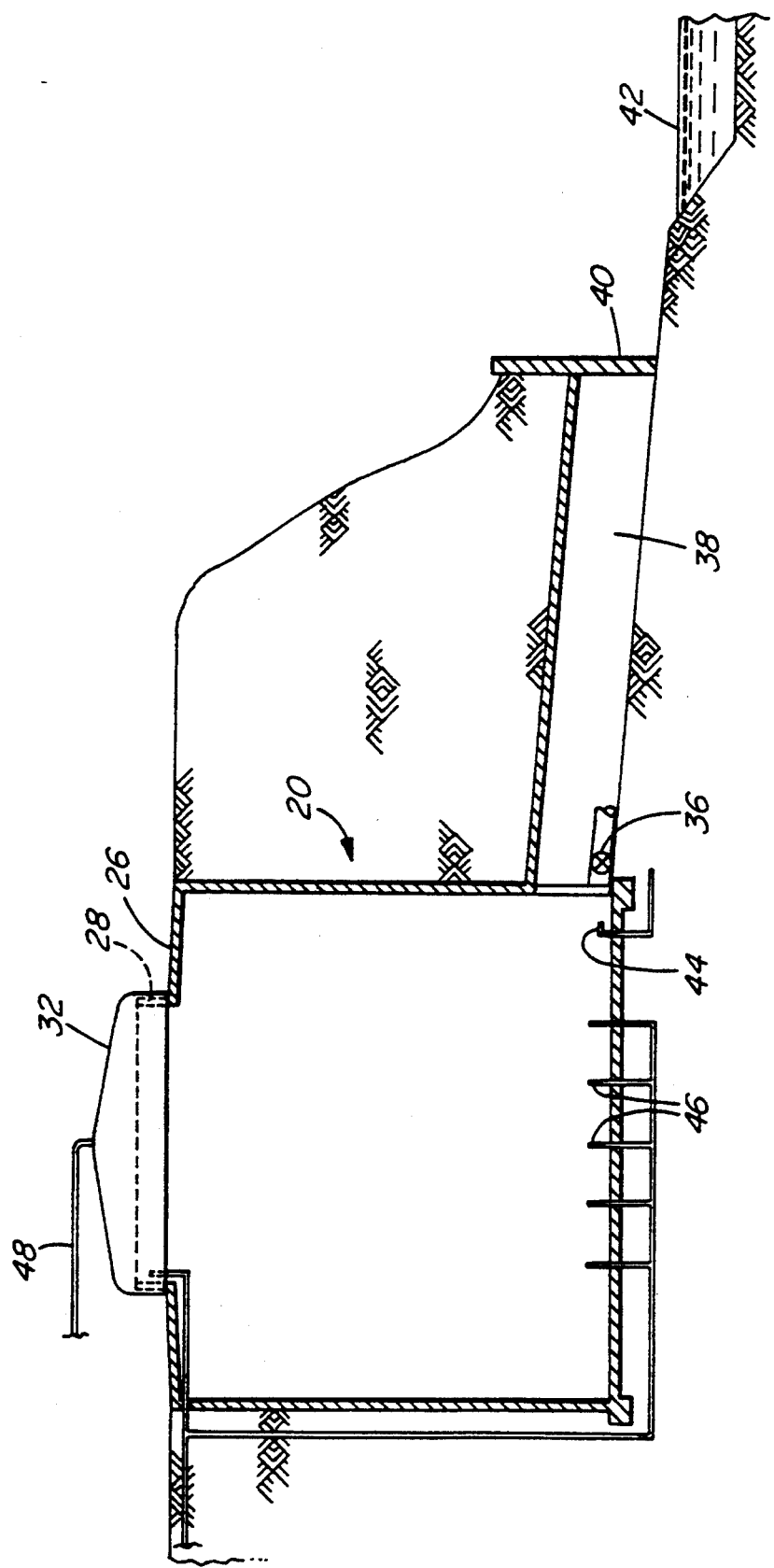
FIG. 8 is a simplified side sectional view of one of the containers and related equipment.
Figure 11:
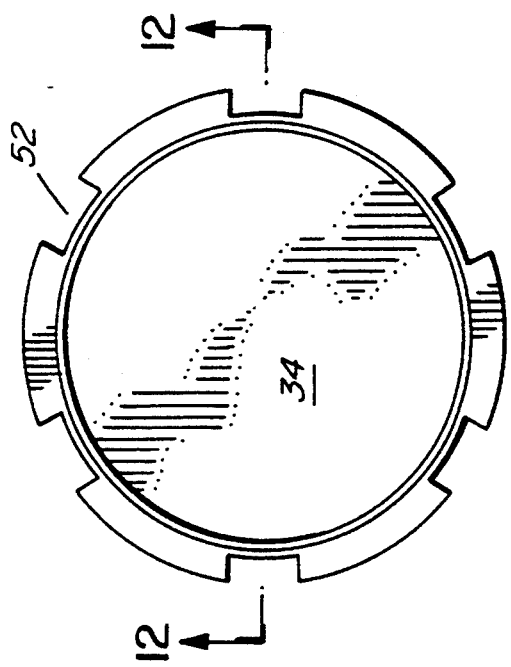
FIG. 11 is a top plan view of one of the doors.
Figure 12:
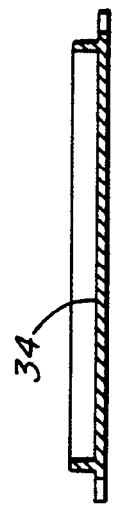
FIG. 12 is a sectional view taken along line 12—12 of FIG. 11.
Figure 9:
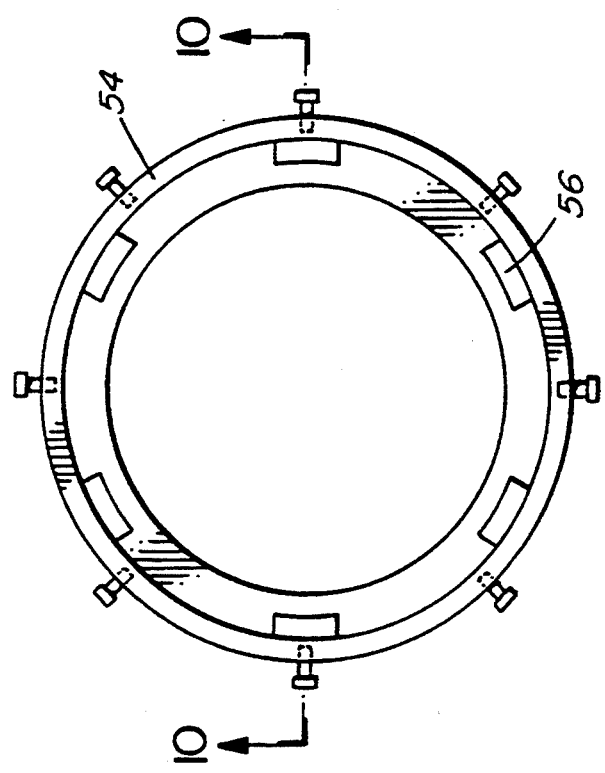
FIG. 9 is a top plan view of the frame for one of the doors thereof.
Figure 10:
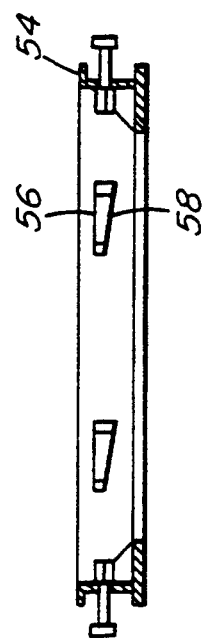
FIG. 10 is a sectional view taken along line 10—10 of FIG. 9.
Figure 13:
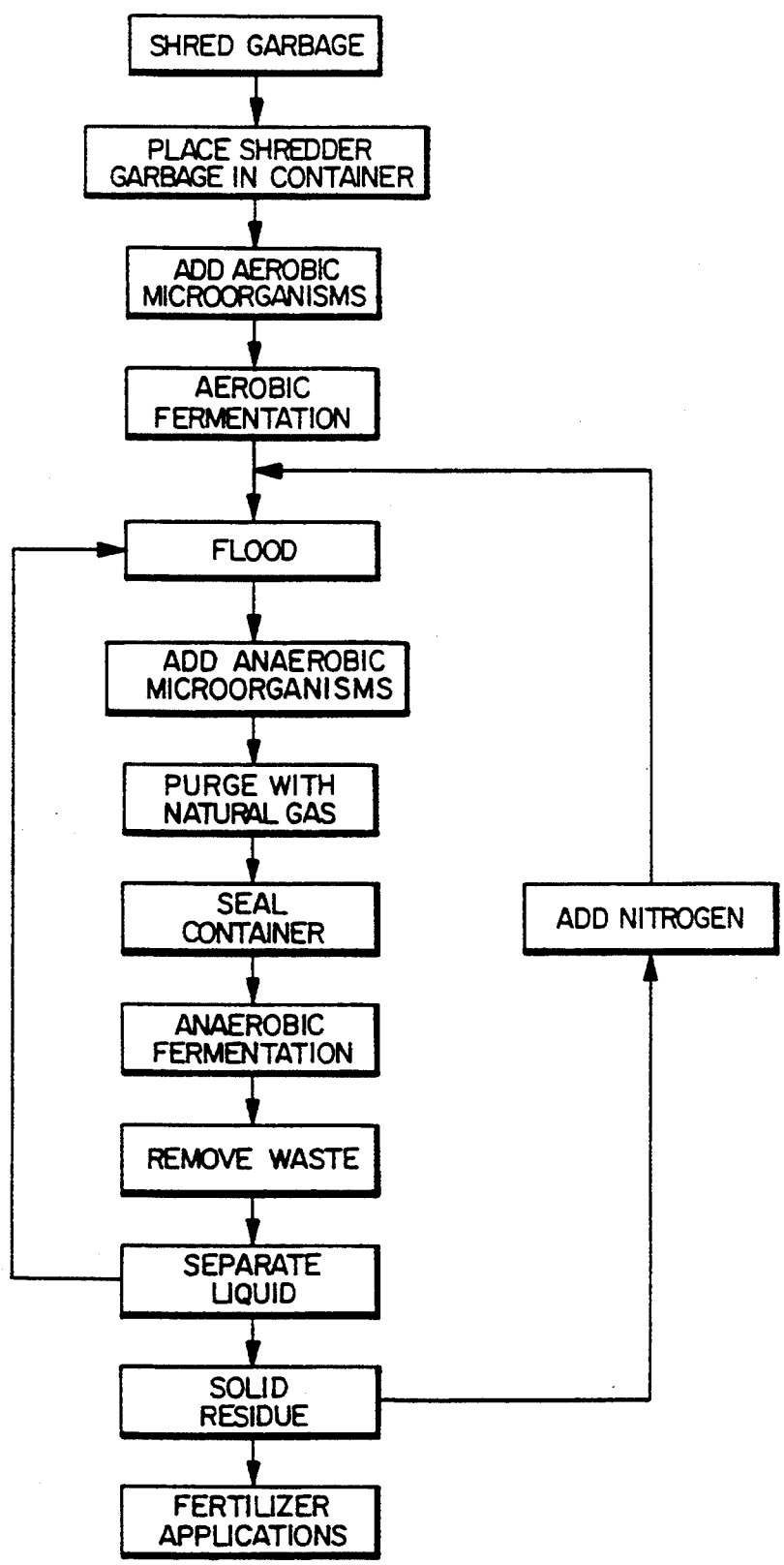
FIG. 13 is a flow chart showing a method of disposing of waste and producing methane according to an embodiment of the invention.

Waste is loaded into the container by means of airtight doors 34 built into the step roof. The doors are dish-shaped, as seen in FIG. 11 and 12 and have a plurality of slots 52 arranged therearound. Each door fits releasably within a frame 54, shown in FIGS. 9 and 10, which has a plurality of interior projections 56, each having an angled bottom 58. There is one projection received in each slot in the door. The projections tighten against the door to hold it securely after the door is placed over the frame and rotated slightly. A clean out valve 36, best shown in FIG. 8, is built into the bottom of the container. Access to the valve is through a service tunnel 38 which also houses an additional door 40 which permits machines to enter the container to facilitate unloading; and clean-up. The residue sludge is emptied into holding ponds 42 where the separation of water from the sludge can take place. A high pressure water nozzle 44 (shown in FIG. 8) is positioned so that the stream will travel through each of the clean out valves so that any obstruction can be readily removed.

High pressure water nozzles 46, shown in FIG. 8, are also built into the inner base of the container. This high pressure water is used for periodic mixing of the fermenting waste.

Removal of oxygen in order to reduce the risk of an explosion is accomplished by feeding natural gas into the container and purging the gases therein through an umbilical hose 48 leading to a manometer 50, best shown in FIG. 1.

Referring to the process itself, the input waste is typically urban, household garbage although the process would be applicable to other types of waste as well. The conversion of the waste is expedited by first shredding the material. The waste is inoculated with aerobic microorganisms during or after the shredding process. These serve a number of important purposes. The first is to break down the cellulose fiber into smaller fractions, later to be an essential food material (nitrogen source) for the subsequent anaerobic fermentation process described also below. Fungi, such as Trichoderma spp and bacteria, such as Cellulomonas spp may be used instead or as well.

The second function of the microorganisms is to heat the mass of the waste to speed the subsequent anaerobic fermentation. The heating in this example is accomplished by the heat of evolution which is defined as the heat given off during the process of the aerobic decay.

The third function of the microorganisms is to increase the nitrogen in the waste prior to the anaerobic process. The anaerobic process requires a carbon/nitrogen ratio of approximately 30:1 which is the approximate ratio of carbon to nitrogen consumed by the anaerobic organisms subsequently employed. However, typical garbage and vegetable matter has a much higher carbon to nitrogen ratio, so steps must be taken to increase the nitrogen.

Initially the nitrogen can be increased by adding solid or liquid residue recovered at the end of the anaerobic process. This is relatively high in nitrogen, typically about 14%. Manure from other sources may be substituted. This is typically done by soil bacteria of the Rhizobium genus acting in a symbiotic relationship with a host plant, usually a member of the family Leguminosae including the sub-orders Papilionaceae, Caesalpinieae and Mimoseae. Three examples of these plants are *Pueraria thunbergiana, Pueraria lobota* and *Leucaena leucocephala*. These examples along with beans, alfalfa and clover are all leguminosae plants.

Some of the bacteria useful in the aerobic process are as follows:

| | |
|---|---|
| Cellulomonas | Micrococcus |
| Streptomyces | Proteus |
| Bacteroides | Rhodeopseudomonas |
| Sarcina | Serratia |
| Clostridium | Pseudomonas |
| Escherichia | Aerobacter |
| Rhizobium | Bacillus |
| Streptococcus | Leptospira |
| Bacillus Sub tilis | Beggaiatoa |

In addition, as discussed above, the fungi Trichoderma spp and Cellulomonas spp may be utilized as well.

The aerobic fermentation and subsequent anaerobic fermentation described below may be enhanced by poisoning out microorganisms which do not contribute to the desired result. This is an opportunity for the use of antimicrobials and, to a lesser degree, selected microbes. In addition, the rate of decomposition may be accelerated by the use of designed bacteria. More efficient strains of bacteria can be developed by, for example, sub-lethal infusions of antibiotics together with organic selection. This yields a stronger bacterial base. This has been accomplished in the past with other bacteria. For example, the bacteria Beggiatoa, a marine bacteria, has been enhanced in order cause decay in garbage bags and other plastic materials. Other strains can render PCB's harmless. The bacteria *Pseudomonas cepacia* has been developed by the University of Illinois Medical School so it can utilize Agent Orange (2,4,5-trichlorophcnoxyacetic acid). The bacteria uses this as the sole carbon source.

The aerobic fermentation continues while the container is filled with garbage, typically a period of time of a week. Once the container is full, the aerobic process continues for a further period of time, typically another week, in order to further degrade the cellulose and build up the heat of the mass as well as the amount of nitrogen. After about one week the container is flooded with an aqueous solution, such as water or liquid residue from the previous cycle. The container is then sealed off from the air. Periodic mixing of the slurry is necessary, at least once a day. In the present embodiment this is accomplished using the high pressure water from the nozzles described above.

After a period of a week, essentially all of the oxygen is consumed so that the system is now anaerobic. However, to reduce the risk of explosion, the container is purged with natural gas which flows through the umbilical hose leading to the manometer described above. After this occurs, the process of anaerobic decomposition can begin. Various microorganisms are useful for this aspect of the method including the following bacterium:

*Methanobacterium formicicum*
*Methanobacterium omelianskii*
*Methanobacterium sphngenii*

*Methanobacterium suboxydans*
*Methanobacterium propionicum*
*Methanococcus vannielii*
*Methanococcus rnazei*
*Methanosarcina Methanica*
*Methanosarcina barkerii*

During the anaerobic degradation, the mixing continues. Methane gas is evolved and is removed from the container, typically for use in commercial or industrial applications. The gas may be held in a holding system prior to use. Once the methanogenic process is completed, and the methane removed, the valves in the drainage tunnel are opened and evacuation of the waste residue takes place. The waste is emptied into a holding pond. The liquid is separated from the solid. The liquid may be rcutilized for flooding the next batch of garbage. A portion of the solid is reutilized for seeding the subsequent batch of garbage with nitrogen. The remainder may be utilized as a nitrogen rich material for use as a natural fertilizer.

It will be understood by someone skilled in the art that many of the details provided above are by way of example and are not intended to limit the scope of the invention which is to be interpreted with reference to the following claims:

What is claimed is:

1. A method of producing methane from urban waste, comprising the steps of:
   shreadding the waste;
   inoculating the waste with nitrogen producing aeroble microorganisms,;
   formenting the waste with the acrobic microorganisms to increase nitrogen levels in the waste sufficiently for anaerobic fermentation thereof;
   further increasing nitrogen control in the waste by the addition of solid or liquid residue selected from the group consisting of manure and leguminosne plants:
   continuing the aerobic fermentation until the carbon/nitrogen ratio is approximately 30:1
   inoculating the waste with anaerobic microorganims;
   placing the waste with anaerobic microorganism;
   placing the waste inoculated with the anaerobic microorganisms in an oxygen free environment and evolving methane from the waste in the oxygen free environment.

2. A method as claimed in claim 1, wherein the waste is exposed to oxygen for one week before placing the waste in the oxygen free environment.

3. A method as claimed in claim 1, wherein the waste is enriched with nitrogen by adding solid residue remaining after the methane is evolved during a previous cycle of said method.

4. A method as claimed in claim 1, wherein the aerobic microorganisms include a bacteria selected from the group consisting of Cellulomonas, Streptomyces, Bactcroides, Sarcina, Clostridium, Escherichia, Rhizobium, Streptococcus, Micrococcus, Proteus, Rhodeopseudomonas, Serratia, Pseudomonas, Aerobacter, Bacillus, Leptospira, and Beggiatoa or Trichoderma fungi.

5. A method as claimed in claim 1, wherein the aerobic microorganism is Cellulomonas spp.

6. A method as claimed in claim 1, wherein the microorganism is the fungi Trichoderma spp.

7. A method as claimed in claim 1, wherein the waste is placed in a container after being shredded.

8. A method as claimed in claim 1, wherein the waste is heated during said aerobic fermentation.

9. A method as claimed in claim 8, wherein the waste is heated by inoculating the waste with bacillus sub tillis.

10. A method as claimed in claim 1, wherein the waste is flooded with an aqueous liquid before being placed in the oxygen free environment.

11. A method as claimed in claim 1, wherein the waste is mixed during the anaerobic fermentation.

12. A method as claimed in claim 1, wherein the waste is at a temperature of 0° C. to 71° C. as the methane is evolved.

13. A method as claimed in claim 1, wherein the waste is at a temperature of 32° C. to 38° C. as the methane is evolved.

14. A method as claimed as claim 1, wherein the mixture is at a pH between 6.8 and 8.0 as the nitrogen evolves.

15. A method as claimed in claim 11, wherein the waste is mixed once a day.

16. A method as claimed in claim 7, wherein the waste is purged of oxygen before evolution of methane begins.

17. A method as claimed in claim 16, wherein the oxygen is purged by natural gas added to the container.